(12) United States Patent
Perroud et al.

(10) Patent No.: US 8,828,736 B2
(45) Date of Patent: Sep. 9, 2014

(54) MICROELECTROPORATION DEVICE FOR GENOMIC SCREENING

(75) Inventors: Thomas D. Perroud, San Jose, CA (US); Ronald F. Renzi, Tracy, CA (US); Oscar Negrete, Livermore, CA (US); Mark R. Claudnic, Livermore, CA (US)

(73) Assignee: Sandia Corporation, Albuquerque, NM (US)

( * ) Notice: Subject to any disclaimer, the term of this patent is extended or adjusted under 35 U.S.C. 154(b) by 678 days.

(21) Appl. No.: 13/173,180

(22) Filed: Jun. 30, 2011

(65) Prior Publication Data

US 2012/0004144 A1    Jan. 5, 2012

Related U.S. Application Data

(60) Provisional application No. 61/360,972, filed on Jul. 2, 2010.

(51) Int. Cl.
*G01N 25/08* (2006.01)
*C12M 1/42* (2006.01)
*B01L 3/00* (2006.01)

(52) U.S. Cl.
CPC ... *B01L 3/502761* (2013.01); *B01L 2300/0864* (2013.01); *B01L 2300/0645* (2013.01); *B01L 2200/0668* (2013.01); *C12M 35/02* (2013.01)
USPC ............... 436/150; 435/287.2; 435/288.5; 436/180; 422/502

(58) Field of Classification Search
USPC ............... 436/150, 180; 435/287.2, 288.5; 422/502
See application file for complete search history.

(56) References Cited

U.S. PATENT DOCUMENTS

2008/0050834 A1 *   2/2008   Pamula et al. ............... 436/86

\* cited by examiner

*Primary Examiner* — Jyoti Nagpaul
(74) *Attorney, Agent, or Firm* — Timothy P. Evans

(57) ABSTRACT

We have developed an microelectroporation device that combines microarrays of oligonucleotides, microfluidic channels, and electroporation for cell transfection and high-throughput screening applications (e.g. RNA interference screens). Microarrays allow the deposition of thousands of different oligonucleotides in microscopic spots. Microfluidic channels and microwells enable efficient loading of cells into the device and prevent cross-contamination between different oligonucleotides spots. Electroporation allows optimal transfection of nucleic acids into cells (especially hard-to-transfect cells such as primary cells) by minimizing cell death while maximizing transfection efficiency. This invention has the advantage of a higher throughput and lower cost, while preventing cross-contamination compared to conventional screening technologies. Moreover, this device does not require bulky robotic liquid handling equipment and is inherently safer given that it is a closed system.

14 Claims, 4 Drawing Sheets

# MICROELECTROPORATION DEVICE FOR GENOMIC SCREENING

CROSS REFERENCE TO RELATED APPLICATIONS

This application claims the benefit of the filing date of U.S. Provisional Application 61/360,972, filed 2 Jul. 2010, entitled "A Microelectroporation Device for Genomic Screening," hereby incorporated by reference in its entirety

STATEMENT OF GOVERNMENT SUPPORT

The United States Government has a paid-up license in this invention and the right in limited circumstances to require the patent owner to license others on reasonable terms as provided for by the terms of contract DE-AC04-94AL85000 awarded by the U.S. Department of Energy to Sandia Corporation.

TECHNICAL FIELD

This invention relates to systems and device for use in the field of gene structure and more particularly the field of mapping genes and sequencing DNA.

BACKGROUND

RNA interference (RNAi) technology has recently emerged as a powerful tool to investigate host proteins involved in virus replication on a genome-wide level (Krishnan, M. N.; Ng, A.; Sukumaran, B.; Gilfoy, F. D.; Uchil, P. D.; Sultana, H.; Brass, A. L.; Adametz, R.; Tsui, M.; Qian, F.; Montgomery, R. R.; Lev, S.; Mason, P. W.; Koski, R. A.; Elledge, S. J.; Xavier, R. J.; Agaisse, H.; Fikrig, E., "RNA interference screen for human genes associated with West Nile virus infection," Nature 2008, v. 455(7210): pp. 242-U67; Brass, A. L.; Dykxhoorn, D. M.; Benita, Y.; Yan, N.; Engelman, A.; Xavier, R. J.; Lieberman, J.; Elledge, S. J., "Identification of host proteins required for HIV infection through a functional genomic screen," Science 2008, v. 319 (5865): pp. 921-926). By systematically silencing >20,000 individual host genes and analyzing their involvement in viral infection, a comprehensive portrait of virus-host interactions can be revealed. The use of this technology has yet to be performed on viral agents requiring BSL-4 biocontainment since traditional high-throughput robotic screening equipment cannot be placed within BSL-4 due to space constraints, aerosol-generation biohazards, and highly restricted access for equipment maintenance. The microelectroporation device described herein addresses these issues through a high-throughput multiplexed microfluidic platform capable of suppressing gene expression using genome-wide RNAi in primary cells upon viral infection.

Two high-throughput formats are currently being used for genome-wide RNAi screening: multiwell plates and microarrays (Carpenter, A. E.; Sabatini, D. M., Systematic genome-wide screens of gene function. Nature Reviews—Genetics, 2004, v. 5(1): pp. 11-22; Erfle, H.; Neumann, B.; Liebel, U.; Rogers, P.; Held, M.; Walter, T.; Ellenberg, J.; Pepperkok, R., "Reverse transfection on cell arrays for high content screening microscopy," Nature Protocols, 2007, v. 2(2): pp. 392-399). The multiwell-plate approach, where each well contains host cells and a different small-interfering RNA (siRNA), requires microliters of costly RNAi reagents, and comes with bulky, robotic screening equipment that requires regular maintenance. Although a smaller well size is possible, significant well-to-well variation caused by evaporation and temperature gradients limit the screening throughput to 384-well plates. The microarray format consists of printing hundreds of siRNA spots onto a glass slide with a microarray spotter device. Cell transfection is achieved by seeding cells on top of the slide. However, the lack of physical barriers between different spots on these microarrays makes this approach prone to cross-contamination and prevents or greatly impedes analysis of secreted factors. Moreover, seeding the cells in this manner results in wide variability in the number of cells distributed at each RNAi spot.

SUMMARY

In one embodiment of the invention, therefore, a device and method for efficiently trapping and distributing cells throughout a large array of sites is disclosed.

Another aspect of the embodiment comprises a method for limiting the number of trapped cells to a statistically significant number thus minimizing the number of costly primary cells used.

Still another aspect of the embodiment is a device having a density of cell collection sites of at least 30 sites per $cm^2$.

Yet another aspect of the embodiment comprises a method to prevent or reduce the potential for cross-contamination between cell collection sites.

Again another aspect of the embodiment comprises a biocompatible gasket which seals and isolates the cell collection sites from each other and from the surrounding environment.

To the accomplishment of the foregoing and related ends, certain illustrative aspects of the claimed subject matter are described herein in connection with the following description and the annexed drawings. These aspects are indicative of various ways in which the subject matter may be practiced, all of which are intended to be within the scope of the claimed subject matter. Other advantages and novel features may become apparent to those skilled in the art from the following detailed description when considered in conjunction with the appended drawings.

BRIEF DESCRIPTION OF THE DRAWINGS

The accompanying drawings illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF ONE OR MORE EMBODIMENTS

Figure 1:
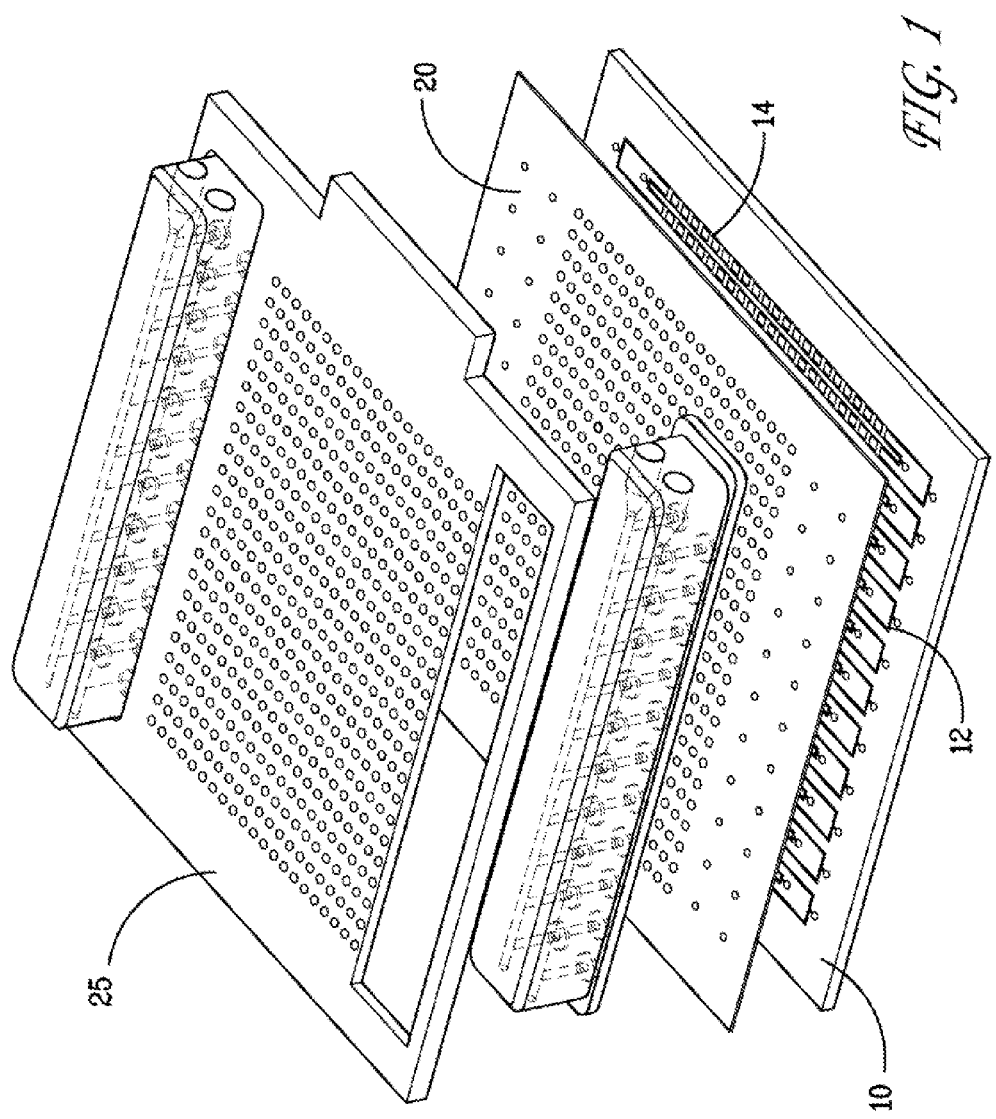
FIG. 1 shows a microelectroporation device comprising an optically transparent substrate coated with an optically transparent conductive oxide with a network of microfluidic channels and an array of microchambers; a biocompatible gasket; and a printed circuit board with discrete, addressable microelectrodes.

Our microelectroporation device ("microelectroporator") is capable of high-throughput screening with thousands of host genes per slide, while minimizing reagent consumption. The density of microchambers (30 microchambers/cm$^2$) on this microelectroporator is an order of magnitude higher than that of conventional 384 well plates (~3 microchambers/cm$^2$). Additionally, this sealed miniaturized device does not require large robotic liquid handling equipment and can be used in biosafety level containment. Our microelectroporator shown in FIG. 1 is comprised of three parts: (1) an optically transparent substrate 10 coated with an optically transparent, conductive oxide cathode with a network of microfluidic channels 12 for cell/reagent delivery and an array of microchambers 14 for oligonucleotides deposition; (2) a biocompatible gasket 25 that ensures fluidic seal between each microchamber and microfluidic channel; (3) A printed circuit board 20 with discrete, addressable microelectrodes (not shown) acting as anodes aligned to each microchambers of the transparent substrate.

Optically Transparent, Electrically Conductive Substrate with Network of Microfluidic Channels Optical transparency is set by the optical properties of the substrate such as plastic, glass or preferably quartz. The network of microfluidic channels is microfabricated in the substrate by etching the substrate using mechanical, dry, or wet etching techniques. To render the substrate electrically conductive while retaining its optical properties, we deposit a transparent, conductive thin layer (~500-800 nm thick) such as indium tin oxide (ITO) onto the substrate. These techniques allow unencumbered optical access to the interior of the device and would be compatible with commercially available scanners for brightfield, fluorescence, or other similar spectroscopic measurements.

Figure 2:
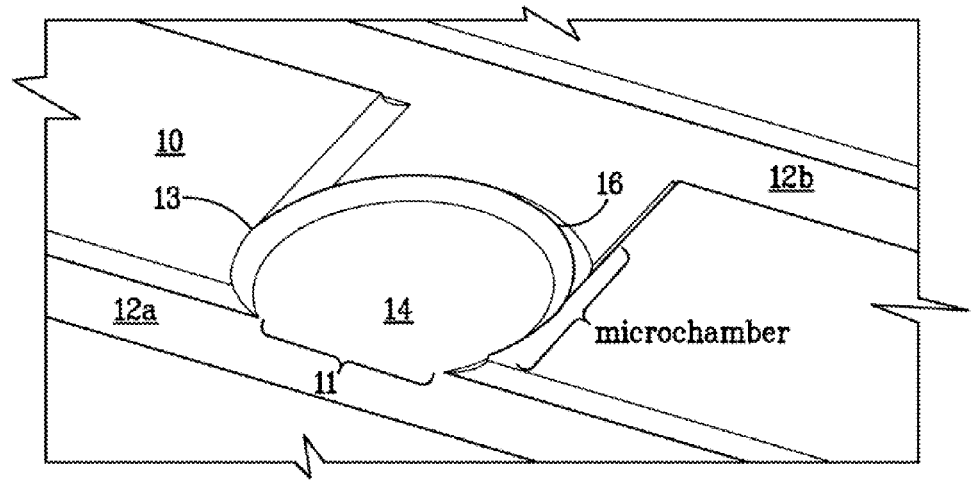
FIG. 2 shows an individual 500-µm-diameter by 30-µm high microchamber.

In this substrate, each siRNA reagent is spotted into individual microchambers as illustrated in FIG. 2 having diameters of about 500 µm. Each of these microchambers 14 comprises a cylindrical cutout in the thickness of substrate 10 on which the microchambers and "supply and "drain" microchannels 12a and 12b are formed. The microchamber is further defined by an opening 11 on one side of the microchamber open to adjacent "supply" microchannel 12a and having surrounding side walls 13 connected by ridge 16 adjacent to "drain" microchannel 12b. The height of the side walls 13 are configured to be about 30-µm and the microchamber, therefore, comprises a total contained volume within the microchamber of approximately 6 nanoliters. By controlling the chamber volume in this way it is possible to achieve approximately 3 orders of magnitude reduction in reagent consumption over conventional multi-well plates.

Following spotting, the microfluidic platform is sealed and can be stored for extended periods. To date, we have found that our platform can be stored for at least 15 months.

Figure 3:
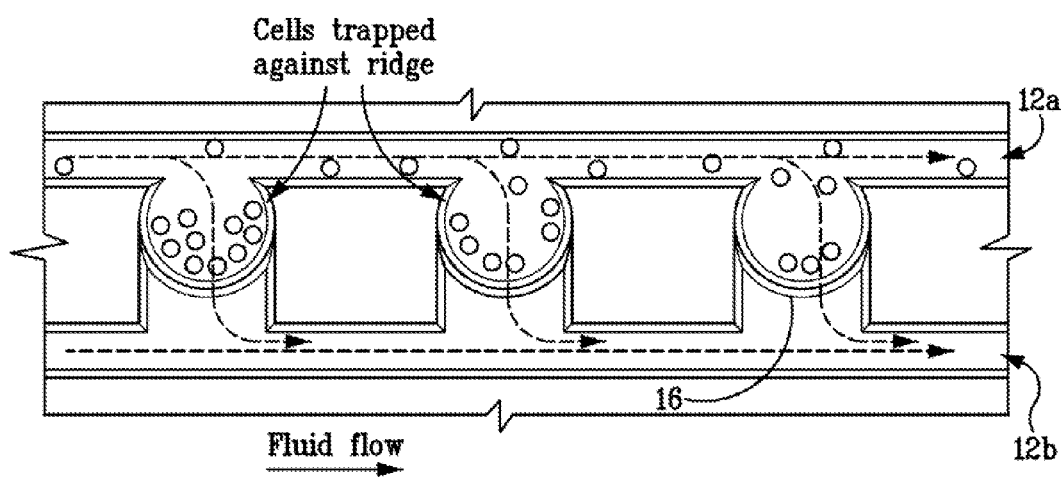
FIG. 3 shows the process of rapid cell loading by trapping cells against a ridge in each microchamber.

As shown in FIG. 3, efficient and rapid cell loading into microchamber 14 is achieved by combining hydrodynamic focusing with hydrodynamic confinement further described in U.S. provisional patent application Ser. No. 61/062,401, now U.S. nonprovisional patent application Ser. No. 12/812,974, herein incorporated by reference. Assuming 10-µm-diameter spherical cells, we estimate that a maximum of 2,500 cells can be trapped in each microchamber against the inside edge of ridge 16. The microchamber and ridge are fabricated by overlapping wet etch fronts as described in "Isotropically etched radial micropore for cell concentration, immobilization, and picodroplet generation," by T. D. Perroud; R. J. Meagher; M. P. Kanouff; R. F. Renzi; M. Wu; A. K. Singh and K. D. Patel, *Lab-On-A-Chip*, 2009, v. (4): pp. 507-515; and described and claimed on International application Serial No. WO/2009/126352 and U.S. application Ser. No. 12/812,986, all herein incorporated by reference. The height of ridge 16 is controlled so as to allow in-flowing liquid from microchannel 12a to go through a 1-to-5 µm, preferably 2-to-3 µm, gap between the top surface of adjacent microchamber wall 13 and an overlaying cover comprised of printed circuit board 20 and biocompatible gasket 25 while preventing cells captured in the microchambers from also passing through. A quantity of several hundreds to thousands of cells per microchamber is a sufficiently large number to acquire statistically significant data (Z factor) while minimizing the number of costly primary cells used. Additionally, cross-contamination between microchambers is minimized by the presence of physical barriers between the spots but also by the fluidic isolation of the microchambers (James, C. D.; Moorman, M. W.; Carson, B. D.; Branda, C. S.; Lantz, J. W.; Manginell, R. P.; Martino, A.; Singh, A. K., "Nuclear translocation kinetics of NF-kappa B in macrophages challenged with pathogens in a microfluidic platform," *Biomedical Microdevices*, 2009, v. 11(3): pp. 693-700).

Biocompatible Gasket for Fluidic Seal

Figure 4A:
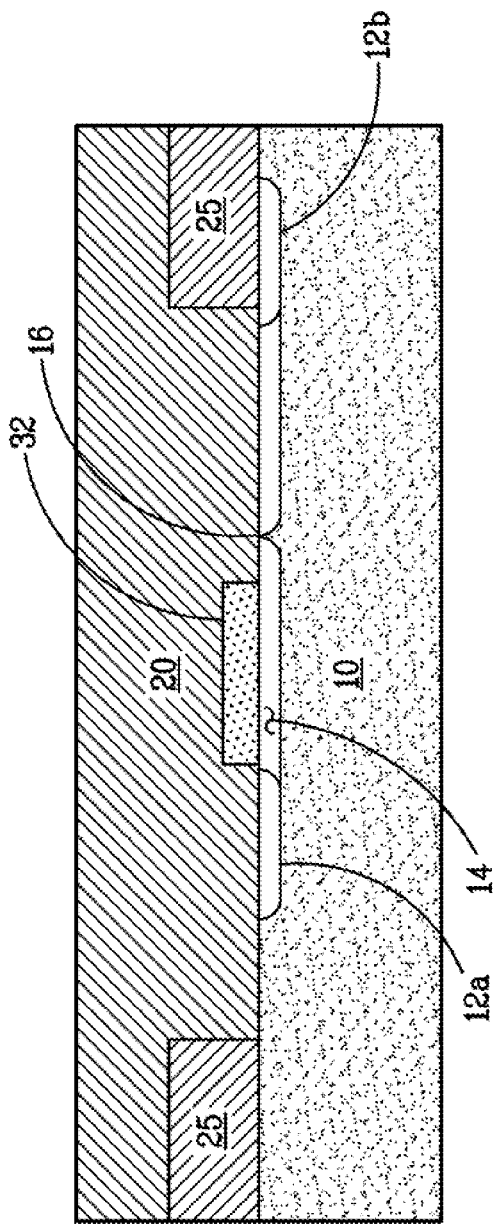
FIG. 4A shows an interface between a microchamber and its corresponding microelectrode to create a precise gap for cell trapping while ensuring fluidic seal and mitigating electrical shorts.
Figure 4B:
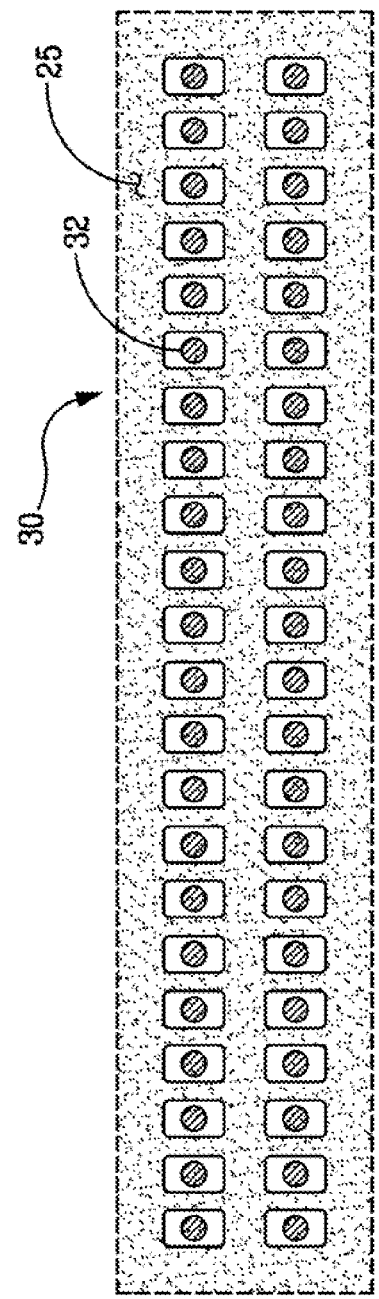
FIG. 4B shows a row of microelectrodes in a printed-circuit board with electrically conductive material located only in the center of the microelectrodes.

As shown in FIGS. 4A and 4B, we have designed a unique interface between the microchamber and an array 30 of corresponding microelectrode 32 that creates a precise gap for cell trapping while ensuring a fluidic seal and avoiding electrical shorts. In order to control the gap between the top of ridge 16 in microchamber 14 and microelectrode 32, the printed circuit board 20 has to be in contact with the edges of the microchamber (two flat incompressible surfaces). The fluidic seal is created by a biocompatible gasket 25 made out of a pressure-sensitive adhesive such as the acrylic adhesives RODERM™ MD-5600 or MD-5800 available from the Rohm and Haas Company (a subsidiary of the Dow Chemical Company, Midland, Michigan), that goes around each microelectrode 32 and which is either die or laser cut. Electrical shorts are avoided by having only the center of the microelectrode containing the electrically conductive material exposed as illustrated in FIG. 4B. The remainder of the electrode surface is covered by a conformal coating such as an acrylic or UV curable formulation. Overall, this interface creates a closed system for increased biosafety.

Printed Circuit Board with Discrete, Addressable Microelectrodes

RNAi transfection is achieved by cell electroporation using a printed circuit board having an array of discrete addressable microelectrodes. Moreover the microelectrode array is configured such that each microchamber in our substrate is juxtaposed to a corresponding microelectrode in the printed circuit board. The board itself is fabricated from FR-4, a NEMA (National Electrical Manufacturers Association) grade designation for glass reinforced epoxy laminate sheet. The PCB is also undercut around the individual microelectrodes forming "islands" that extend out a short distance to match the thickness of the adhesive layer. Moreover, the height of the individual microelectrodes is precisely controlled by using a lapping process.

Each microelectrode is individually addressable enabling rapid optimization of electroporation conditions. To maximize the efficiency of RNAi transfection while minimizing cell death, an optimal electrical field strength of several hundreds of V/cm is used during electroporation (Jain, T.; McBride, R.; Head, S.; Saez, E., "Highly parallel introduction of nucleic acids into mammalian cells grown in microwell arrays," *Lab-on-a-Chip,* 2009, v. 9(24): pp. 3557-3566). A key feature of our device is the short distance between the electrodes (~30 μm) again by controlling the height of each microelectrode by undercutting the PCB thickness around the individual microelectrodes and then lapping the islands formed thereby and the microelectrodes to a specific height above the undercut surface of the PCB. The subsequent potential gradient across these electrodes (~1 V) is lower than that of water electrolysis (1.23 V at room temperature) which, in turn, prevents the generation of hydrogen at the anode—a chemical process known to induce cell death.

Figure 5A:
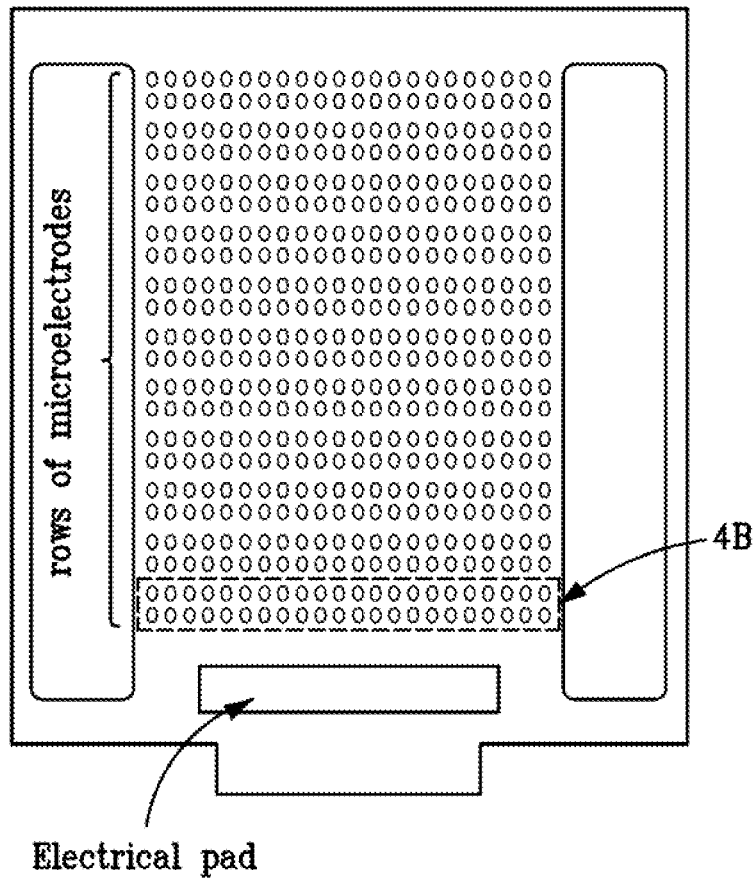
FIG. 5A shows an electrical pad that connects to the indium-tin oxide (ITO) coated substrate.
Figure 5B:
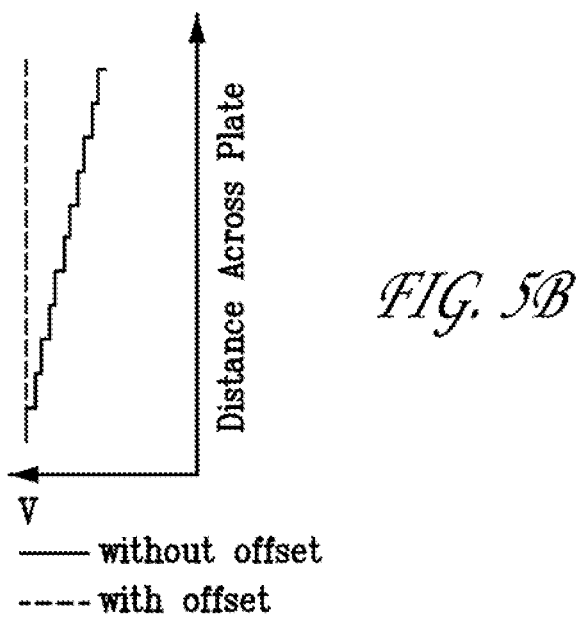
FIG. 5B shows that a uniform electrical field can be maintained across the entire electrical pad shown in FIG. 5A and therefore the entire surface of the substrate by applying a voltage offset to each subsequent row of microelectrodes.

Additionally, unlike previous designs (op. cit. such as shown in Jain, T., et al., *Lab-on-a-Chip,* 2009, v. 9(24): pp. 3557-3566), our microelectroporator is capable of generating a uniform electrical field across the entire plate, thus improving the precision of the results. A right balance has to be found for ITO-coated surfaces between optical transparency and electrical conductivity. The more optically transparent the surface is, the less electrical conductive it becomes (and vice-et-versa). As shown in FIG. 5, we connect to the ITO surface of the coated substrate using a rectangular electrical pad parallel to the first row of microchambers. Knowing the electrical resistivity of the ITO-coated surface (several ohm/square) and subsequently offsetting the voltage of each subsequent microelectrode row, it is possible to produce identical electrical fields having predefined field strengths in every individual microchamber. Although not shown, one skilled in the art would recognize that a low voltage power supply would be necessarily connected across the ITO cathode layer and each of the plurality of microelectrodes in order to provide the electrical potential for electroporation.

Therefore, an improved device has been developed for conducting cell transfection/electroporation. Furthermore, to the extent necessary to understand or complete the disclosure of the present embodiment of the invention, all publications, patents, and patent applications mentioned herein are expressly incorporated by reference therein to the same extent as though each were individually so incorporated.

Having thus described exemplary embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein, but is only limited by the following claims.

We claim:

1. A microelectroporation device, comprising:
   an optically transparent substrate;
   a printed circuit board (PCB);
   a biocompatible gasket disposed between and fluidically sealing a bottom surface of the PCB to a top surface of the optically transparent substrate; and
   a low voltage power supply;
   wherein the optically transparent substrate comprises a networked plurality of microfluidic channels and one or more arrays of microchambers formed into the top surface of the optically transparent substrate, and a conductive metal oxide layer deposited over the top surface to provide a common electrode,
   wherein the PCB comprises an array of discrete, addressable microelectrodes disposed on the bottom surface of the PCB configured and patterned to align with each of the one or more arrays of microchambers to provide a single microelectrode adjacent to each one of the microchambers, and wherein a thickness of the PCB is removed from surface comprising the array of addressable microelectrodes around each of the microelectrode in order to provide clearance for the biocompatible gasket; and
   wherein the biocompatible gasket comprises an array of through-holes configured to match both the array of microelectrodes and the one or more arrays of microchambers thereby providing for fluid and electrical communication between each one of the microchamber and the single microelectrode adjacent thereto.

2. The microelectroporation device of claim 1, wherein the low voltage power supply connected between the conductive metal oxide layer and each of the plurality of microelectrodes.

3. The microelectroporation device of claim 1, wherein conductive metal oxide layer comprise indium tin oxide (ITO).

4. The microelectroporation device of claim 3, wherein the ITO layer is between about 500-800 nm thick.

5. The microelectroporation device of claim 4, wherein the ITO layer is preferably between about 600-700 nm thick.

6. The microelectroporation device of claim 1, wherein the networked plurality of microchannels is further comprised of pairs of parallel microchannels formed into the optically transparent substrate wherein each pair of microchannels is separated by a narrow strip of the optically transparent substrate having a height equal to the depth of the microchannel.

7. The microelectroporation device of claim 6, wherein a uniform linear array of microchambers is formed into each of the plurality of narrow strips of the optically transparent substrate wherein each microchamber is as deep as the height of the narrow strip within which it is formed.

8. The microelectroporation device of claim 7, wherein the height of each of the narrow strips is about 30 μm.

9. The microelectroporation device of claim 7, wherein each of the plurality of microchambers is comprised of a slot shaped cut-out in the narrow strip connecting the pairs of microchannels wherein one end of the slot is comprised of a pair of semi-circular walls that open into a first of the adjacent pair of microchannels (a supply channel) and a semi-circular ridge connecting the pair of semi-circular side walls that is adjacent to a second of the pair of microchannels (a drain channel), wherein the height of the pair of semi-circular side walls is configured to be as high as narrow strip, and wherein the connecting ridge is about 1 to 5 micron lower in height than the height of the surrounding side walls, thereby allowing fluid communication between the supply and drain channels.

10. The microelectroporation device of claim 9, wherein each of the microchamber semi-circular side walls and connecting ridge comprise a diameter of about 500 μm.

11. The microelectroporation device of claim 1, wherein biocompatible gasket comprises a pressure sensitive adhesive.

12. The microelectroporation device of claim 1, wherein the applied voltage at room temperature across the anode and cathode electrodes is less than 1.23 volts.

13. The microelectroporation device of claim 12, wherein the applied voltage at room temperature across the anode and cathode electrodes is about 1 volt.

14. The microelectroporation device of claim 1, wherein a uniform electric field is applied and maintained across the top surface of the optically conductive substrate.

* * * * *